United States Patent [19]

Provonchee

[11] Patent Number: 4,588,555

[45] Date of Patent: May 13, 1986

[54] DEVICE FOR USE IN CHEMICAL REACTIONS AND ANALYSES

[75] Inventor: Richard B. Provonchee, Camden, Me.

[73] Assignee: FMC Corporation, Philadelphia, Pa.

[21] Appl. No.: 432,506

[22] Filed: Oct. 4, 1982

[51] Int. Cl.$^4$ .............. G01N 21/07; G01N 33/52; G01N 35/00

[52] U.S. Cl. .................. 422/72; 422/56; 422/58; 422/64; 422/100; 436/45; 436/166; 436/169

[58] Field of Search .................. 422/55–58, 422/72, 100, 101, 64; 436/44, 170, 809, 166, 45, 169

[56] References Cited

U.S. PATENT DOCUMENTS

| | | | |
|---|---|---|---|
| 3,607,093 | 9/1971 | Stone | 436/97 |
| 3,768,978 | 10/1973 | Grubb et al. | 422/100 |
| 3,784,358 | 1/1974 | Drake, Jr. et al. | 422/56 |
| 3,985,032 | 10/1976 | Avakian | 422/101 |
| 4,046,514 | 9/1977 | Johnston et al. | 436/166 |
| 4,059,020 | 11/1977 | Avakian | 422/101 |
| 4,144,306 | 3/1979 | Figueras | 422/56 |
| 4,178,153 | 12/1979 | Sodickson | 422/58 |
| 4,190,533 | 2/1980 | Hirs | 210/793 |
| 4,234,316 | 11/1980 | Hevey | 422/58 |
| 4,258,001 | 3/1981 | Pierce et al. | 436/170 |
| 4,308,028 | 12/1981 | Elkins | 422/100 |
| 4,331,650 | 5/1982 | Brewer et al. | 436/809 |
| 4,340,480 | 7/1982 | Pall et al. | 210/500.2 |

FOREIGN PATENT DOCUMENTS 52769  6/1982  European Pat. Off. ............ 422/72

Primary Examiner—Barry S. Richman
Assistant Examiner—C. M. Delahunty
Attorney, Agent, or Firm—E. G. Horsky; C. Egolf; E. G. Seems

[57] ABSTRACT

A device and method of making and using the same in performing manual and automated chemical reactions and analyses of clinical assay mediums. Such device including a solid, microporous element formed of adsorbent material and having walls defining an internal cell structure comprised of interconnecting cells within which is contained a precise, measured quantity of reagents.

3 Claims, 13 Drawing Figures

DEVICE FOR USE IN CHEMICAL REACTIONS AND ANALYSES

This invention relates to liquid chemical reactions, and particularly to an improved method and device for use in chemical analyses of assay mediums.

In general, the teachings of this invention are applicable for use in all liquid chemical reactions in which precise, measured quantities of reagents are reacted, and are especially useful in the analyses of assay mediums; that is, the substances to be analyzed for one or more analytes, such as environmental, industrial, biological, and clinical specimens, where accurate, consistent, and, very often, rapid results are essential. In view of the exacting requirements of clinical chemistry analyses, to best illustrate the merits of the present invention, and for the sake of simplicity and ease of description, the present invention is hereafter described as utilized in this field, and including its application with automated clinical chemical analyzers.

The teachings of the present invention are useful in improving known manual clinical chemical analysis systems which often lack sensitivity, particularly in qualitative testing as, for example, when contacting a reagent impregnated fibrous member with a liquid sample, and in the case of quantitative testing where results are highly dependent upon degree of care and skill of the performing technician. Significantly, the present invention is particularly useful with and serves to improve the function of automated clinical chemistry analyzer systems which provide for accurate results and are capable of performing complex analyses. With known automated clinical chemistry analyzers, procedures involved include: (a) sample pickup with dilution, if required, and delivery; (b) separation of proteins and analytes, as by filtration or dialysis; (c) addition and mixing of at least one reagent with the sample and, if appropriate, incubation of the mixture; (d) detection of reactions, for example, by visible or UV (ultraviolet) light or fluorometry; and (e) presentation of reaction data, such as on a strip chart, printed tape, recorder or at a computer terminal. The invention here disclosed is particularly useful in connection with steps (a), (c) and (d) noted above, and thus the following description is generally confined to and emphasizes the applicability of the invention in connection with such analysis steps.

Analyzers presently available employ continuous flow or discrete sample analyses or centrifugation principles, and it is with discrete centrifugal analyzers that the present invention is especially useful.

Representative of such centrifugal analyzers is the GEMENI ™ analyzer manufactured by Electro-Nucleonics, Inc. which employs a disposable 20-place cuvette or rotor disc formed of transparent ultraviolet (UV) light-transmitting plastic material. This disc consists of an outer ring containing twenty cuvettes and a concentric inner ring containing twenty wells, with the cuvettes and wells being aligned radially on the disc. After manually pipetting samples and liquid reagents into respective cuvettes and wells, the disc is placed in the analyzer. In disc loading, one cuvette contains only distilled water another contains only a liquid reagent, and still another contains a standard solution, while samples are pipetted in the required number of the remaining cuvettes. Upon rotation of the disc within the analyzer, the liquid reagents in the disc wells are propelled radially outward into the respective aligned cuvettes and mixed with the standard solution in the one instance, and the samples in the remaining of such aligned cuvettes.

In general, known automated centrifugal and other discrete clinical analyzers are limited in their potential to perform chemistry analyses. Such limitations can be attributed to the inability of the known analyzers or instruments to dispense a variety of different reagents. Moreover, in preparing these known analyzers for use, reagents are reconstituted manually, after which the instruments are "primed" with liquid reagents. Once so prepared, these known instruments are capable of analyzing a batch of serum samples for a single constituent or analyte. However, single sample or stat testing and profiling require interruption of batch analyses or multiple batch runs, with one run for each test in the profile and with multiple manual liquid reagent preparations and changeovers.

Regardless of whether automated centrifugal or other discrete analyzers are employed in batch or single sample testing, the problems encountered in the manual preparation and handling of liquid reagents are aggravated by the need for accurate pipetting of such liquid reagents into retaining wells, cups, or rotors of such instruments. The reagents utilized in clinical analyses are often unstable and if not used promptly, sometimes within a workday, they must be discarded. Certainly the waste of expensive reagents and time, and the potential for significant error in the manual preparation and dispensing of liquid reagents are deficiencies which must be at least minimized for the sake of efficiency and confidence in clinical chemical analyzers. Accordingly, a primary object of this invention is the provision of improved and more satisfactory method and device for conducting liquid chemical reactions or analyses of assay mediums.

Another object is the provision of an improved method and device for conducting manual or automated chemical analyses which facilitate the introduction of precise, measured quantities of one or more reagents into assay mediums for qualitative, and more especially, exacting quantitative determination of analytes.

A still further object is a method of making improved reagent delivery devices which is rapid and, if desired, readily automated, and provides devices containing a precise, measured quantity of reagent with a high degree of consistency.

By this invention, the need to reconstitute reagents in other than unitized amounts and the pipetting of liquid reagents, as is generally required with manual, as well as conventional automated chemical analysis systems, together with the waste of excess or unstable liquid reagents inherent in such reagent preparation and delivery procedures, are completely avoided. Aside from facilitating chemical analyses with known instruments with greater ease, speed, and accuracy in results, the present invention enables known automated analyzers to perform analyses beyond their intended capacity.

As heretofore mentioned, although not limited thereto, the present invention is especially adapted for use with automatic centrifugal clinical chemical analyzers which, of course, must produce precise quantitative results rapidly and accurately. Also as heretofore described, in methods practiced with and devices employed in known automatic centrifugal chemical analyzers, at least one solid or reconstituted liquid reagent is supplied to a well and subsequently and automatically the reagent and an assay medium are mixed for reaction, the reaction detected, and the reaction data presented. The terms "well" and "cuvette" as employed herein refer to any means which may contain reagents individually and/or during mixing and reaction or for detection of a chemical reaction; that is, while reading of reaction results by an automated analyzer. Thus, such well or cuvette may be a test tube or the like, or simply a depression in the surface of a generally rigid surface.

The device of the present invention serves to accurately deliver precise quantitative amounts of reagents in analytical procedures, including procedures requiring reagents which when mixed together react with each other or become unstable and lose their potency over a period of time. Of particular importance, and as heretofore mentioned, is that the present invention can be adapted for use in carrying out a wide variety of chemical analyses, not only in the field of clinical chemistry, but in chemical research, water analysis, and chemical process control. The invention is well suited for use in chemical testing of body fluids such as blood, serum, and urine, since in this work a large number of repetitive tests and profile analyses are frequently conducted and these results are needed within a short time after the sample is taken. The device can be used, for example, in carrying out quantitative analyses for many of the blood components which are routinely measured. Thus the device can be adapted for use in the analyses of such blood components as albumin, bilirubin, urea nitrogen, serum glutamicoxalacetic transaminase, chloride, total protein, glucose, uric acid, acid phosphatase and alkaline phosphatase.

More specifically, the device of this invention includes a solid, microporous element having walls defining an internal cell structure comprised of interconnecting cells, at least some of which open along exposed surfaces of the element. As the element is microporous, and thus has cells or voids, and may well be flexible and compressible, the term "solid" means that the element, in its relaxed state, has a definite structure; that is, its external dimensions define a certain volume, with a portion of such volume being comprised of cells or voids. This element is intended to receive and retain liquids, yet yield the same when appropriate, and thus is formed of adsorbent material and one which is or is adapted to be rendered wettable by the liquid it is to receive. That is, when such liquids are at least in part water, hereinafter referred to as "aqueous mediums," the walls defining the internal cell structure are hydrophilic. The material forming such element must also be inert with respect to the liquids it is to receive which may be, for example, a sample to be assayed, a sample diluent, one or more reagents, which may or may not be reactive with each other, or any combination of liquid samples, diluents, and reagents, and desirably is at least translucent, so that in certain applications reaction results can be determined with conventional optical readers.

Suitable for use in forming such element are a variety of materials, such as glass, metals, and especially organic polymers, referred to herein as organoplastics, including high density polyethylene (HDPE), polypropylene (PP), polyvinylidenefluoride (PVDF) fluorocarbon. Those of such materials which are normally hydrophobic can be subjected to an oxygen plasma or a corona discharge treatment or other known procedure to render the walls forming the element cell structure hydrophilic for use with aqueous mediums.

The configuration and size of the cells or voids of the element and the total void volume thereof are not critical. The voids may range, for example, from about 1 micrometers ($\mu$m) to 1 mm. in diameter and, as they open or interconnect, their sizes and/or configurations may well vary. Yet, elements having a generally uniform volume of voids can be readily achieved and may range from, for example, about 10% to 60% of the volume of the element. Obviously, the smaller the size of the voids, the more tenacious is the liquid retention by the surface tension and/or interfacial forces present, and as the void volume of the element is increased so is its liquid-receiving capacity. Solid, microporous materials which are suitable for use in preparing the described element are available from Porex Technologies of Fairburn, GA and Chromex Chemical Corporation of Brooklyn, NY.

The preparation of such elements as a reagent carrier merely involves applying a predetermined volume of aqueous liquid reagent, which may be comprised, for example, of polar or non-polar liquid(s), such as water, alcohols, ketones, acids, etc., which serve as carriers and have a precise, measured quantity of reagent dissolved or dispersed therein, onto the solid microporous element, whereupon the liquid rapidly enters into the internal cell structure thereof by wicking or capillarity. The element is sized to contain a void volume at least equal to, and preferably greater than, the volume of applied liquid so that essentially all of the liquid reagent is contained within the element cell structure. Thus, as the volume of applied liquid contains a precise, measured quantity of reagent, so also does the element which contains such liquid.

After receiving the liquid reagent, the element generally feels dry to the touch, requires no extraordinary care during handling, and may be used without further treatment or may be packed in air-tight bags or the like for future use in this condition. Alternatively, and preferably, the liquid-treated elements may be air, lyophilized or oven, or vacuum dried to remove carrier liquid(s) and, particularly with elements of small cell size, gentle tumbling of the elements during the drying process does not result in any apparent loss of reagent. Drying of the treated element is rapid as liquid is wicked from within the elements to the surfaces thereof as such surfaces are dried, leaving the reagent behind as a solid within the cell structure, as by adherence to the walls defining the interconnecting cell structures. The term "solid" as applied to the reagent is employed herein as meaning the reagent is in a non-flowable condition.

In lieu of applying the liquid reagent to individual elements, it may be applied to solid, microporous material in sheet or other form, which is subsequently cut, either before or after drying, into elements each containing a predetermined, precise, measured quantity of reagent. The application of the liquid reagent, either to individual elements or to a solid, microporous sheet, may be achieved, for example, by pipetting, spraying, dipping, or the like.

A plurality of reagents may be contained within a single element, with reagents which are non-reactive with each other being simultaneously or sequentially applied thereto, and with interacting reagents being applied to areas of the elements that are isolated from each other, as by physical separation or by contact of the element with a heated blade or the like to collapse and fuse a narrow area of its structure into a liquid-flow barrier.

The device of the present invention may consist of the solid, microporous element by itself or attached to some means by which the element may more conveniently be manipulated or better perform its function. For example, an element having a predetermined void volume may be attached to one end of a pipette so as to project therefrom and, when dipped into a liquid, such as an aqueous sample to be assayed or a diluent, will assume a known volume thereof by wicking. Such assumed liquid may be subsequently separated from the element, as under the pressure of air or other fluid or under a vacuum introduced or applied at the opposite end of the pipette or by centrifugation.

When serving as a reagent carrier, the element may simply be attached to one end of a dip stick or the like for use in making a qualitative determination of analytes that may be present in an assay medium. Such element may be also immobilized or supported within an open container, such as a test tube, at a location removed from its closed end and the reagent separated from the element by centrifugation. If the reagent is contained as a solid in such carrier element, it is liquified; that is, dissolved or dispersed within an appropriate liquid, such as water, alcohols, ketones, acids and the like, as heretofore mentioned, which may also serve as a diluent and/or to liquify a sample to be assayed, prior to the application of the centrifugal force. With the sample to be assayed and liquid reagent within the test tube and mixed together, the chemical reaction is simply detected and the qualitative results determined and recorded by conventional apparatus. Alternatively, the reagent in the element may be dissolved or dispersed in a liquid, the test tube then centrifuged, and the liquid contents thereof put into a cup or cuvette or a conventional discrete analyzer for use with an assay medium.

In use with a rotor disc of a conventional automated centrifugal analyzer which, as heretofore described, includes a series of cuvettes arranged adjacent to the disc periphery and a corresponding series of wells aligned radially with such cuvettes, a carrier element need only be placed and retained in one of such wells, the reagent therein dissolved or dispersed within an appropriate liquid, such as an aqueous medium, after which the analyzer is operated in its normal fashion. A diluent or a liquid sample which is to be assayed may be applied to the carrier element whether or not liquification of a dried reagent is required. Otherwise, at least the assay medium is placed in the cuvette aligned with such one well. Under the centrifugal force developed by rapid rotation of the rotor disc, the liquid reagent within the carrier element is rapidly separated from such element and is propelled into the aligned cuvette where it is thoroughly mixed and reacted with the assay medium. The reaction results are then determined and presented by the analyzer. It is intended, of course, that the carrier element remain within the one well during application of the centrifugal force and, if necessary, is restrained therein by any suitable means which will not retard the flow of liquid, as by the geometry of the well or an adhesive or weighted porous cover or screen.

By providing each of a series of the wells in the rotor disc with a carrier element containing the same reagent, single sample or stat tests on a batch of samples may be performed concomitantly. Alternatively, a carrier element containing a different reagent may be provided within each of such series of wells to perform a profile analysis; that is, a series of different analyses of the same liquid sample.

As employed herein, "reagents" are chemically active materials which, when released from the carrier element, combine with each other and/or one or more constituents of an assay medium to provide an intermediate or final product having chemical characteristics different from the reagents and/or assay medium prior to the combining thereof. For example, reagents may react only with the analyte to be determined when such reagent is combined with the assay medium, while still other reagents, when dissolved or dispersed in a liquid, such as an aqueous medium, may react to provide a solution having a pH, salt concentration, or buffering capacity necessary for reacting with one or more constituents of an assay medium.

Any liquid-soluble or liquid-dispersible reagents may be incorporated into the carrier elements, and for use in clinical chemical analyses, may include, for example, enzymes, enzyme substrate, antibodies, antigens, haptens, inorganic and organic reagents, buffers, salts, and the like, as well as radio-actively tagged or fluorescent reagents of the foregoing types, including nonisotopic types, such as enzymes, cofactors, lumniscent agents, and the like.

Further, the term "adsorbent," as employed herein in connection with the material forming the solid, microporous element, is intended to make clear that reagents contained within such elements do not penetrate into the material itself; that is, are not absorbed as in the case of a paper or other fibrous reagent carrier. In solid form, the reagent is contained within the cell structure of the carrier element, as by adherence to the walls thereof and/or as entrapped particles, and when dissolved or dispersed within an aqueous medium or other appropriate liquid is essentially completely separated from the carrier element when a force, such as centrifugal force, air pressure, or like, is applied thereto.

As with conventional rotor disc, the discs described herein are preferably formed of clear plastic or other material which transmits UV light to enable detection of chemical reactions by conventional automatic chemical analyzers. When formed of thermoplastic material, the rotor discs may be shaped with desired wells, cuvettes, and flow channels by a simple thermomolding process.

In the drawing, FIG. 1 is a perspective view diagrammatically illustrating, on an enlarged scale, a microporous, open cell element of the present invention;

For simplicity, reference is made in the following detailed description to reagents which are soluble or dispersible in aqueous mediums; that is, mediums which, at least in part, include water.

Figure 1:
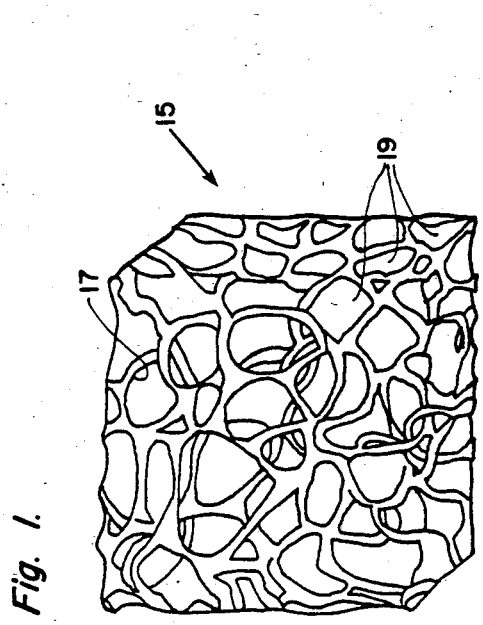

Shown in FIG. 1 is a solid, microporous element 15 having walls 17 defining an internal cell structure comprised of interconnecting cells or voids 19. As heretofore mentioned, such voids may range from about 1 micrometer to 1 mm. in diameter and thus FIG. 1 diagrammatically illustrates the element 15 on a greatly enlarged scale for clarity and ease of description. The element 15 is formed of adsorbent material which is inert to liquids and solids with which the element is intended to subsequently contact, and polypropylene, for example, is suitable for such use. If necessary, the element 15 is subjected to a treatment such as an oxygen plasma or corona discharge treatment, to render the walls 17 thereof hydrophilic.

Figure 2:
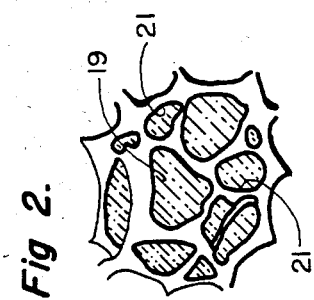
FIG. 2 illustrates a fragmentary portion of the element shown in FIG. 1 having a liquid reagent contained in the cells thereof.

Shown in FIG. 2 is a portion of the element 15 having contained in the cells 19 thereof a liquid reagent 21 which is comprised of an aqueous medium in which is dissolved or dispersed a precise, measured amount of reagent. The reagent carrier element shown in part in FIG. 2 may be used as such, may be packaged for future use, or may be lyophilized or air, oven, or vacuum dried to remove the aqueous medium, leaving the reagent contained within the element cells 19 as, for example, by adherence to the walls, as shown at 23 in FIG. 3.

Figure 3:
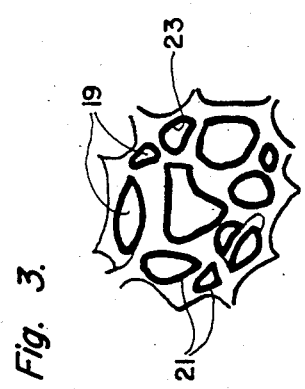
FIG. 3 is a view similar to FIG. 2 in which a precise, measured quantity of reagent is contained within the cells of the microporous element.
Figure 4:
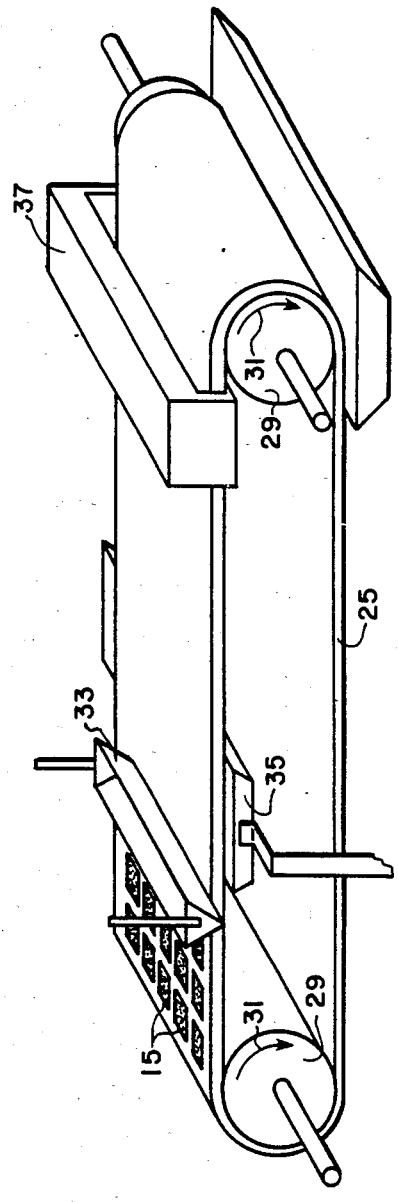
FIG. 4 is a perspective view diagrammatically illustrating a method of providing a microporous element as shown in FIG. 1 with a reagent as shown in FIGS. 2 and 3.

Reagent carrier elements, as referred to in connection with FIGS. 2 and 3, may be formed by merely pipetting a predetermined volume of liquid reagent onto an element 15 of desired size and void volume. An automated system is illustrated in FIG. 4 wherein such elements 15 of predetermined size and void volume are laid onto an endless belt conveyor 25 which is of porous construction and is trained about rollers 29, at least one of which is driven as indicated by arrows 31. An aqueous liquid having a precise, measured quantity of reagent dissolved or dispersed therein is applied onto the elements 15 as the conveyor 25 carries them beneath a spray head 33. Preferably the amount of liquid reagent delivered to the elements 15 is such as to essentially fill the cells 19 thereof, and thus, knowing the void volume of the element 15, the precise, measured amount of reagent contained within the cells 19 of such element 15 is also known. The conveyor 25 is porous and is formed of glass filaments or other normally hydrophobic material so that the excess liquid reagent may readily pass through such conveyor and into a collection trough 35.

The reagent carrier elements, which are as shown in FIG. 2, are ready for use or may be packaged in this condition for future use, or may be dried as by passage through an oven 37 to evaporate the aqueous medium and leave the reagent contained within the element cells 19, as by adherence to the walls 17 thereof, as shown at 23 in FIG. 3.

Figure 5:
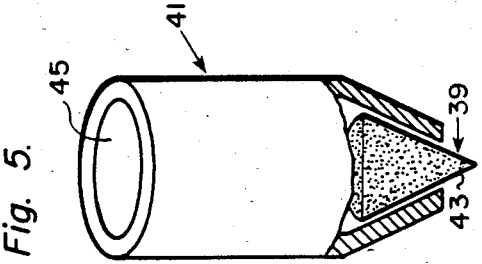

The element 15 shown in FIG. 1 is adapted for various uses in connection with clinical chemical analysis systems. For example, the element 15 may be shaped as a cone 39 as shown in FIG. 5 and be applied to a pipette 41. By merely contacting the exposed portion 43 of the conical element 39 with an aqueous medium, such as a sample, a diluent, assay medium, or reagent, the element 39 will rapidly wick a volume of such aqueous medium essentially equal to its void volume. Separation of the aqueous medium thus assumed from the element 39 may be achieved, for example, by introducing air into the end 45 of the pipette 41. The element 39 may be disposed and, after pipette cleansing, another element 39 may be inserted for reuse of this device. While reference has been made to a pipette 41, it is intended that the term "pipette" include a syringe and the like which may be similarly equipped with a disposable element 39 for use as described above. It will be apparent, of course, that the entire device shown in FIG. 5; that is, the element 39 and pipette 41, may be disposable as a unit, if desired.

Figure 6:
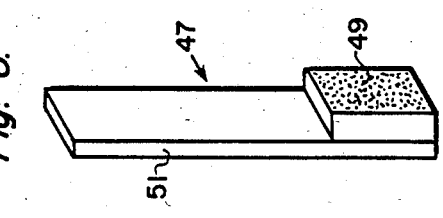

Particularly useful for qualitative analyses is the device 47 shown in FIG. 6 wherein a reagent carrier element, such as shown in FIGS. 2 and 3 and indicated at 49, is attached to a support 51 which is formed of a material, such as polypropylene, which is inert and non-absorbent and, preferably, transparent or translucent. The device 47 may be used in a manner as are conventional dipstick test units in which a reagent is impregnated into a paper or other fibrous member or to deliver a reagent into a liquid sample. Thus, the user needs only to immerse the reagent carrier element 49 within an aqueous assay medium, as for example, a urine sample, and detect in the element 49 evidence of a chemical reaction, such as a color change. Unlike the conventional fiber pad dip sticks, the carrier element 49, having a known void volume, not only contains a known quantity of reagent, but will take up a precise and known amount of aqueous assay medium. Further, as the carrier element, on a macro scale, is quite uniform and is at least translucent, conventional optical instruments may be employed to detect and read reaction results. Alternatively, by means of the support 51, the carrier element 49 may be agitated within the aqueous assay medium to release the reagent therefrom and into the assay medium, with evidence of a chemical reaction being detected, for example, by a change in the color of the assay medium itself.

An important advantage of the device 47 is that the precise, measured quantity of reagent contained within the element 49 is completely dissolved or dispersed and mixed with the aqueous assay medium, and thus accurate test results are obtained. This advantage is absent, of course, when using a conventional fiber-impregnated reagent carrier for the user is never sure as to the amount of reagent that is released or reacted with the aqueous assay medium.

Figure 7:
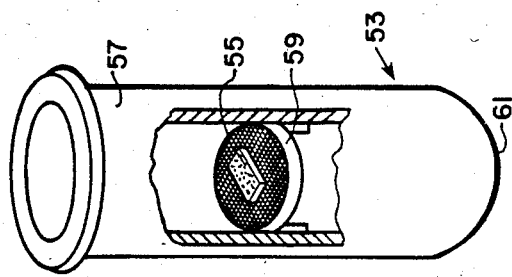
FIGS. 5-13 illustrate different modifications of devices of the present invention which incorporate elements as shown in FIG. 1 or reagent carrier elements as shown in part in FIGS. 2 and 3.

A further device of this invention is shown at 53 in FIG. 7 wherein a reagent carrier element 55 is supported within a test tube 57, as by a plastic screen 59, against movement toward the closed end 61 of the test tube 57. The screen 59, or other suitable support means, may be frictionally or otherwise retained in place so as to permit the liquid reagent to flow from the reagent carrier element 55 toward the closed end of the test tube 57 upon being separated from such element 55 as by centrifugal force.

In using the device 53, an aqueous medium, such as a diluent or assay medium, is introduced into the test tube 57 and onto the element 55 to dissolve or disperse, if necessary, the precise, measured quantity of reagent contained within such element 55. If the aqueous medium so applied to the element 55 is something other than the assay medium, such assay medium may be first introduced into the test tube 57 and collected at its closed end 61. The test tube 57 is now centrifuged to separate the dissolved or dispersed liquid reagent from the element 55 and propel the same into and mixed with the assay medium, if such is present. Alternatively, the collected liquid reagent may be delivered to a cup or cuvette of a conventional automatic clinical chemistry analyzer for assay analysis. Detection of the chemical reaction and presentation of reaction data is achieved by use of conventional equipment.

Figure 8:
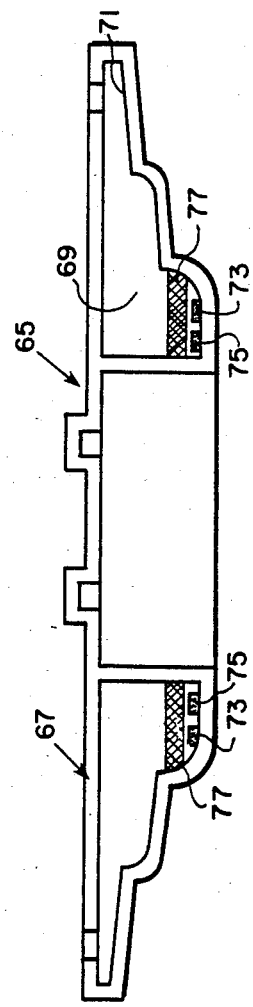

The device 65 shown in FIG. 8 includes a conventional transparent rotor disc 67 as employed with known automatic centrifugal chemical analyzers, such as the GEMINI TM analyzer heretofore described, that includes a series of separated wells 69 for containing reagent carrier elements and a like number of cuvettes 71, each being aligned radially with an individual reagent well 69. In accordance with the teachings of the present invention, one or more reagent carrier elements, such as the elements 73 and 75 illustrated, are retained within the reagent wells 69, as by a screen 77, if necessary. In this illustrated embodiment precise, measured quantities of different reagents are contained within the respective elements 73 and 75, and, if the reagents in such elements are reactive with each other, there is no risk of such reaction in view of the physical separation of these elements.

Employing the improved device shown in FIG. 8, with known automatic centrifugal clinical chemical analyzers enables simplified profile chemistry analyses to be obtained. In the use of the device or rotor disc shown in FIG. 8, with the reagent wells 69 having fixed therein the appropriate reagent elements 73 and 75, a technician need only add an appropriate amount of aqueous mediums, which may be a liquid assay medium, into each of such wells 69 to dissolve or disperse the reagents and thus providing a reconstituted combined reagent of precise concentration. Samples or assay mediums, if not already delivered to the wells 69, are then pipetted into the respective cuvettes 71, after which the device is placed in the known automatic centrifugal clinical chemical analyzer which functions in its ordinary manner to rotate the device, causing the reagents to flow radially from the wells 69 and into the cuvettes 71 so as to mix and react with the samples or assay mediums therein. Such known analyzers will then automatically detect the reaction and present the reaction data.

Figure 11:
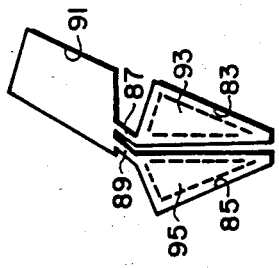
Figure 9:
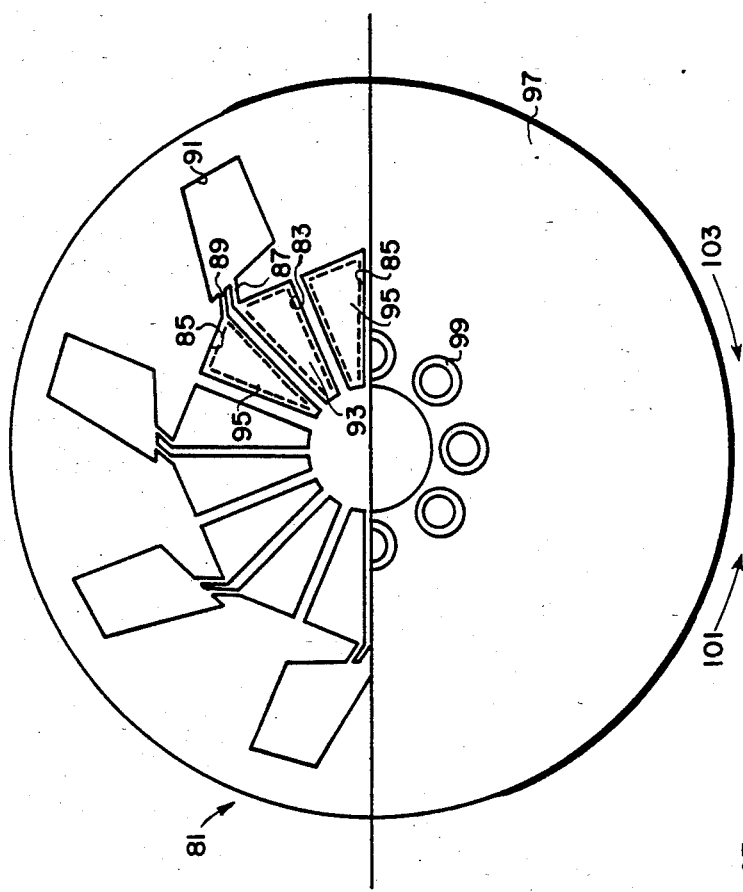
Figure 10:
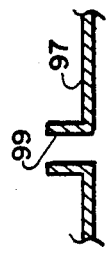

A modified rotor disc 81, also formed of transparent material, is shown in FIGS. 9-11 and includes a series of separated wells, such as indicated at 83 and 85 for containing reagent-carrier elements, with each pair of such wells 83 and 85 communicating by channels 87 and 89 with a single cuvette 91 which is aligned generally radially therewith. Reagent-containing elements 93 and 95, which may contain, for example, precise, measured quantities of reagents which are reactive with each other, are disposed within the separate wells 83 and 85, and are retained therein by a disc cover 97 having standpipes 99 which overlie and are adapted for use in delivering an aqueous medium, such as a liquid assay medium or a diluent, into the wells 83 and 85 and thereby dissolve or disperse the reagents contained within the elements 93 and 95.

In the use of the rotor disc 81, the precise, measured quantity of reagent contained in the respective elements 93 and 95 is dissolved or dispersed within an aqueous medium, say an aqueous assay medium, introduced into the wells 83 and 85 through a cover standpipe 99. This loaded disc 81 is then placed in a conventional automatic clinical chemistry analyzer and rotated in either of the directions indicated in FIG. 9 by the arrow 101 and 103, whereby the liquid reagents and assay medium are separated by centrifugal force from the elements 93 and 95 and propelled through the channels 87 and 89 into the cuvette 91 where they are mixed, as by intermittent rotation of the disc 81 in opposite directions 101 and 103, and reacted. As the disc 81, being also formed of transparent material, the cuvette 91 serves also as a reading chamber with the chemical reaction detected and recorded with conventional equipment.

It will be noted that the channels 87 and 89 and the walls of the cuvette 91 are arranged as to encourage liquid flow from the wells 83 and 85 during rotation of the disc 81 in the direction of the arrow 101 and, during intermittent rotation of the disc 81 in the opposite directions, encourage mixing within the cuvette 91 while inhibiting flow into the wells 83 and 85. It will be understood that the disc 81 may be utilized with only a single of such reagent carrying elements 93 and 95 and, as mentioned above, that the cuvette 91 serves both as a mixing and reading cell.

Figure 13:
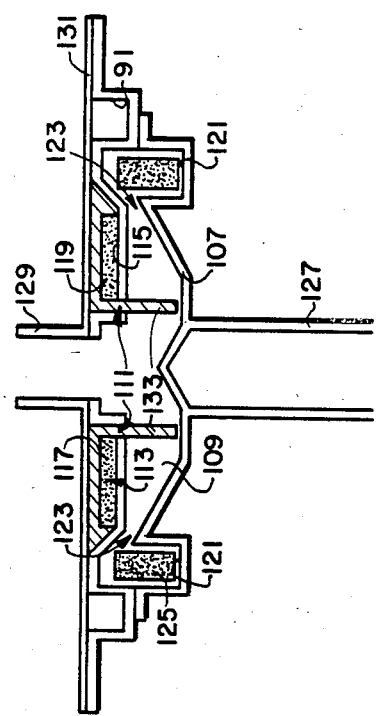
Figure 12:
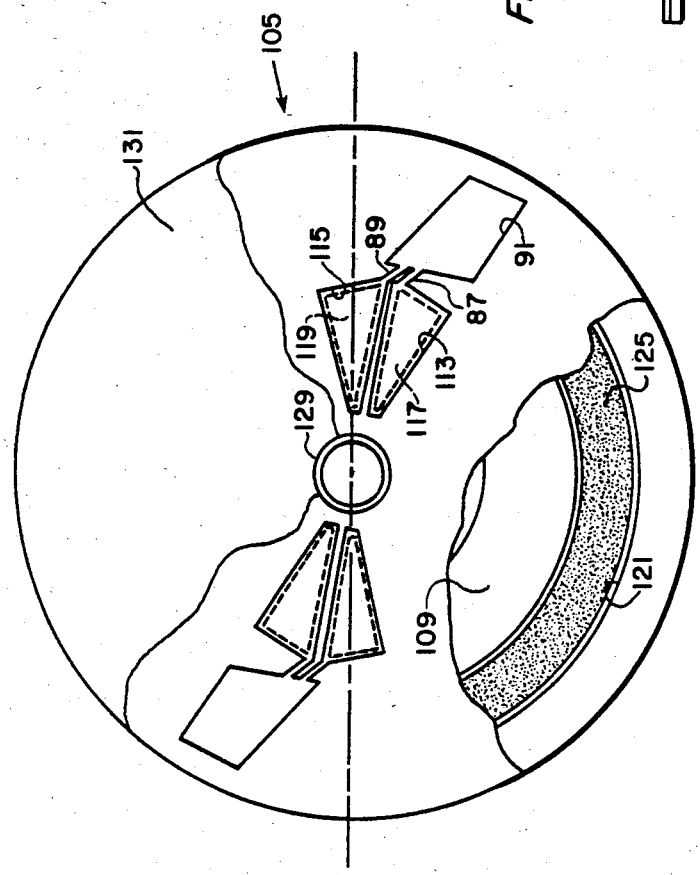

The rotor disc embodiment 105 shown in FIGS. 12 and 13 includes wells, cuvettes, and channels which correspond to the like structures shown in FIGS. 9-11. However, in this embodiment, the bottom wall 107 of the disc 105 is depressed to form a central chamber 109, which communicates by openings 111 with wells 113 and 115 within which are disposed reagent carrying elements 117 and 119, and, also, an annular pocket 121 which communicates at 123 with the chamber 109. Desirable, but not necessarily, a ring 125 of porous material, which may be fibrous, is disposed within the pocket 121. A collar 127 depends from the disc bottom wall 107 for reception of a spindle of a conventional automatic clinical chemical analyzer, and a second collar 129 projects from the top wall 131 of the disc 105.

An aqueous medium, such as a liquid assay medium is delivered through the collar 129 into chamber 109 and, by wicks 133 immersed in such liquid and engaged with or are part of the reagent carrying elements 117 and 119, is delivered by capillarity or wicking to such elements to dissolve or disperse the precise, measured quantities of reagents therein. This loaded disc is then placed in a conventional automatic analyzer, and rotated first in one and then intermittently in the opposite directions as described in connection with the disc 81. During the initial of such rotation, excess liquid medium in the chamber 109; that is, such liquid not wicked into the elements 117 and 119, is collected by the porous ring 125, for discard.

As all elements 117 and 119 are supplied with a common liquid medium, such as an aqueous assay medium, from the chamber 109, the rotor disc 105 is especially adapted for profile analyses.

The following example is provided to still further illustrate the merits of the present invention. Solid, microporous elements, such as shown in FIG. 1, formed of polyethylene and normally hydrophobic, were subjected to a conventional oxygen plasma treatment at 100 watts and 0.5 torr for five minutes which rendered the walls defining the cell structures of the elements very hydrophilic. Mention is made that with solid, microporous elements having a thickness not greater than about 1/16 inch, a conventional corona discharge treatment is equally satisfactory for rendering the cell walls hydrophilic.

The elements, having dimensions of 10×40×1.2 mm, was then each loaded with 50 $\mu$L of each of the four liquid reagents, including a buffer, substrate, coenzyme, and coupling enzyme, which are necessary for performing a BUN (blood urea nitrogen) analysis. Some mixing of the reagents occurred during the application thereof, and the void volume of the elements exceeded the total volume (200 $\mu$L) of the applied reagents, as evidenced by the absence of surface liquid. The loaded elements felt dry to the touch, and were then dried in a hot-air oven. Elements dried at 30° C. for a period of 45 minutes had a moisture content of 10.5%, while others dried at 45° C. for 30 minutes had a moisture content of 3%. In comparison, like amounts of the same reagents dried on flat non-absorbent plastic chips required drying periods of 4 hours at 30° C. and 6 hours at 45° C. to attain the respective moisture contents of 10.5% and 3%. As the dried reagents are within the cell structuring of the elements, they were physically protected and could withstand rather rough handling without harm to the elements or loss of reagent.

Individual elements dried at 30° C. for three hours were supported within separate test tubes by hydrophobic plastic spacers and flooded with 0.8 mL of water. Reagent dissolution was rapid and after about 2 minutes, the test tubes were centrifuged at about 2000 RPM for about two minutes. The liquids recovered in the respective test tubes were then poured into assay cups of a Chemetrics automatic clinical chemistry analyzer, commercially available from the Chemetrics Corporation, Burlingame, CA, and a BUN assay was run using standards of 40, 40, 20, 20, 80, 80. A copy of the print out tape from the analyzer showing the results is made part of this disclosure as "BUN ASSAY TEST RESULTS".

```
            BUN ASSAY TEST RESULTS
            01 WATER CAL 30.16° C.
         GAIN                    9
         OFST                  590
         FULL                  795
         ABS0                807.0
         CALDTA              25557
            02 STANDARD-01
         −0.350Δ              1.468Y
         FACTOR =             114.3
         ZICEPT =              0.00
         QUALITY=               100
            03 SAMPLE-01 30.25° C.
            −0.384Δ 1.392Y 100%
                43 MG/DL ABN
            04 SAMPLE-02 30.25° C.
            −0.200Δ 1.465Y 100%
                22 MG/DL ABN
            05 SAMPLE-03 30.25° C.
            −0.195Δ 1.428Y 100%
                22 MG/DL ABN
            06 SAMPLE-04 30.25° C.
            −0.698Δ 1.262Y 100%
                79 MG/DL ABN
            07 SAMPLE-05 30.25° C.
            −0.739Δ 1.300Y 100%
                84 MG/DL ABN
            ERROR SUMMARY:
         IN ERROR               0
         NONLINEAR              0
         ABNORMAL               5
         NORMAL                11
```

I claim:

1. A device for use in liquid chemical reactions comprising a disc adapted to be rotated about its axis, containing (i) a mixing cuvette, within which an assay medium and at least one reagent-containing liquid may be mixed for chemical reaction;

(ii) a solid microporous element located between the cuvette and the disc axis and having walls defining an internal cell structure with interconnecting cells, at least some of which open along exposed surfaces of the element;

(iii) a precise measured quantity of reagent contained within the cell structure of the microporous element, the reagent being in solid form yet capable of being solubilized or dispersed in a liquid to form said reagent containing liquid and the element being formed of a material that is inert and adsorbent with respect to the reagent and that is wettable by the said reragent-containing liquid;

(iv) a first liquid delivery means for facilitating flow of said reagent-containing liquid from the microporous element to the cuvette, by the action of centrifugal force on said reagent-containing liquid in the element upon rapid rotation of the disc in at least one direction about its axis; and (v) a second liquid delivery means, consisting of a chamber in the disc for containing a liquid and a wick extending from said microporous element and into said chamber, for delivery of said liquid from the chamber into the element and into contact with the reagent by capillarity or wicking for forming said reagent-containing liquid, the chamber being at a location in the disc remote from the cuvette.

2. In a centrifugal chemical analyzer including a rotor disc having a mixing cuvette within which an assay medium and at least one liquid reagent are mixed together for chemical reaction upon rotation of the rotor disc about its axis, means for rotating the disc about its axis, means for detecting the chemical reaction between the assay medium and the liquid reagent, and means for presenting the reaction data, the improvement in the rotor disc which comprises (i) a well in the rotor disc at a location between the disc axis and the mixing cuvette;

(ii) a solid microporous element contained within the well and having walls which define an internal cell structure with interconnecting cells, at least some of which open along exposed surfaces of the element;

(iii) a precise measured quantity of reagent contained within the cell structure of the microporous element, the reagent being in solid form yet capable of being solubilized or dispersed in an aqueous liquid to form a reagent-containing liquid;

(iv) a first delivery means for facilitating delivery of said reagent-containing liquid from the microporous element into the cuvette via propulsion under the influence of centrifugal force during rotation of the rotor disc in at least one direction about its axis, and (v) a second delivery means, for delivering an aqueous liquid into the well for dissolving or dispersing reagent in the element and thereby forming said reagent-containing liquid said second delivery means consisting of a chamher in the rotor disc, a wick extending from the microporous element and into the chamber for delivery of an aqueous liquid from the chamber into the element and into contact with the reagent by capillarity, an annular pocket formed adjacent to and communicating with the outer periphery of the chamber for receiving excess liquid from the chamber by centrifugal force upon rotation of the rotor disc in one direction about its axis, and a ring formed of porous solid material for containing the excess liquid received within the annular pocket.

3. In a centrifugal chemical analyzer including a rotor disc having a mixing cuvette within which an assay medium and at least one liquid reagent are mixed together for chemical reaction upon rotation of the rotor disc about its axis, means for rotating the disc about its axis, means for detecting the chemical reaction between the assay medium and the liquid reagent, and means for presenting the reaction data, the Improvement in the rotor disc which comprises
(i) a well in the rotor disc at a location between the disc axis and the mixing cuvette;
(ii) a solid microporous element contained within the well and having walls which define an internal cell structure with interconnecting cells, at least some of which open along exposed surfaces of the element;
(iii) a precise measured quantity of reagent contained within the cell structure of the microporous element, the reagent being in solid form yet capable of being solubilized or dispersed in an aqueous liquid to form a reagent-containing liquid;
(iv) a first delivery means for facilitating delivery of said reagent-containing liquid from the microporous element into the cuvette via propulsion under the influence of centrifugal force during rotation of the rotor disc in at least one direction about its axis; and
(v) a second delivery means, for delivering an aqueous liquid into the well for dissolving or dispersing reagent in the element to form said reagent-containing liquid, said second delivery means consisting of a chamber in the rotor disc communicating with the well and a standpipe protruding through a cover on the rotor disc and communicating with the chamber.

* * * * *